United States Patent [19]

Green et al.

[11] 4,032,785
[45] June 28, 1977

[54] TIRE INSPECTION MACHINE PRESENTING AN X-RAY IMAGE OF THE ENTIRE WIDTH OF THE TIRE

[75] Inventors: Donald T. Green, Mentor, Ohio; Edward de Benedetti, San Jose, Calif.

[73] Assignee: United States Steel Corporation, Pittsburgh, Pa.

[22] Filed: Mar. 28, 1974

[21] Appl. No.: 455,544

[52] U.S. Cl. .......................................... 250/358 T
[51] Int. Cl.² ...................................... G01N 23/00
[58] Field of Search ........ 250/358, 359, 360, 358 T

[56] References Cited

UNITED STATES PATENTS

| | | | |
|---|---|---|---|
| 3,789,226 | 1/1974 | Green et al. | 250/360 |
| 3,793,526 | 2/1974 | Collmann et al. | 250/360 |
| 3,809,900 | 5/1974 | Steffel | 250/360 X |
| 3,903,416 | 9/1975 | Fox | 250/358 T |

Primary Examiner—Davis L. Willis
Attorney, Agent, or Firm—Harold S. Meyer

[57] ABSTRACT

An X-ray machine for production line inspection of tires places each tire in turn with one sector of the tire inside of a U-shaped arrangement of three fluorescent screens so that one screen faces the tread and the other two face the sides of the tire. An X-ray source inside the bead circle of the tire produces X-ray shadow pictures on the screens, which are separately viewed by a video camera, with an image of the picture on each screen transferred to a third of the target of a storage tube, so that a composite image of the entire width of the tire sector can be displayed on a picture tube. The tire is rotated stepwise for display of still pictures of every sector of the tire.

9 Claims, 16 Drawing Figures

TIRE INSPECTION MACHINE PRESENTING AN X-RAY IMAGE OF THE ENTIRE WIDTH OF THE TIRE

CROSS REFERENCES

This invention in its preferred form includes the X-ray Inspection System of U.S. Pat. No. 3,758,723, and many elements of the X-ray Tire Inspection Machine of U.S. Pat. No. 3,789,226, both owned by the assignee of this application.

BACKGROUND

Machines for X-ray inspection of manufactured products have involved display of the X-ray shadow picture, produced on a fluorescent screen, on picture tubes by means of closed circuit television. This makes it possible for the inspector to be in a convenient location, close enough for control but out of range of the hazard of exposure to the X-rays.

In the case of products as complex in shape as pneumatic tires, it has been found to be impossible to scan the entire structure with X-ray beams in fewer than three zones. Consequently, it has been necessary to relocate a single X-ray system for three or more successive scans, or to use multiple X-ray systems with more than one picture tube or monitor, which generally requires more than one operator, or else a very slow operation.

The principle object of this invention is to provide equipment for display on a single television monitor of an X-ray picture of a complete band across a tire from one bead over the sidewalls and the tread or crown to the other bead.

Other objects are to simplify the construction and operation of X-ray tire inspection equipment, and to provide rapid and reliable inspection of the entire structure of each tire by a single operator.

SUMMARY OF THE INVENTION

In accordance with this invention in its preferred form, a sequence of tires is supplied on a conveyor for automatic successive placement in a location with the wall of the tire between an X-ray source or sources and plural imaging systems for adjoining zones of the tire. The imaging systems are preferably three in number, one for the tread or crown portion of the tire, and one for each side portion including a sidewall and a bead. The three X-ray shadow images so produced are then combined into a single picture, with the center portion and the two side portions each including a sufficient part of the width so that no part is omitted, and the composite picture is displayed on the picture tube of a television monitor.

Preferably each picture is a still picture so as to avoid any blurring of fine details by reason of persistence of moving images or by reason of near coincidence of exposure intervals with the time between successive appearances of details in the same part of the field of view. After a brief display of the still picture for determination by the operator of presence or absence of objectionable irregularities or other defects, it is replaced by another still picture of the next crosswise band in a progression around the circumference of the tire. The operator is given a brief rest during removal of the tire and its replacement by the next tire.

The essential new features of this invention are the combination of separate images into a single composite picture of the entire width of the tire, and provision of means for producing such a composite picture. There are several ways in which this can be done.

Generally it is expedient to provide three fluorescent screens, one for the crown portion and the other two for the two sidewall portions on either side, either in a fixed location or in a fixed relationship to one another, since the fluorescent screens are the largest elements of the imaging system. The bringing together of the three images into a single picture can be accomplished by provision of three television cameras with their electronic images suitably juxtaposed into a single picture. Alternatively, a single television camera can receive the three images successively and transmit them to a single storage tube.

The presently preferred arrangement involves a single X-ray tube with its beam directed successively toward three fluorescent screens, with the three X-ray shadow pictures reflected successively into the optical axis of a single television camera in a fixed position. This assures uniform brightness and magnification and also protects the somewhat sensitive camera tube from mechanical shocks and other disturbing influences. The three distinct images are then successively transferred, each to one-third of the width of the target of a storage tube from which the composite picture is read for display on the picture tube of the monitor as a still picture.

There are various possible arrangements of mirrors for reflecting the three fluorescent shadow pictures into the optical axis of the camera tube. The basic requirements for this purpose are that the optical paths be essentially identical in length for uniform magnification and proper focus, and that the number and direction of reflections be such as to present the three images in the proper relation without angular shift which would present them out of the proper relationship to one another. A complete 180° reversal is not troublesome because the image can be reversed, side to side or upside down as may be required, by the use of suitable conventional circuitry in transferring the particular part-image from the camera tube to the appropriate part of the target of the storage tube. An angular shift is easily avoided by keeping the optical axis, no matter how many times reflected, always in a single plane.

The preferred arrangement accordingly is to provide three fluorescent screens with the lateral screens at an angle of about 60° to the plane of the central screen, with a tire so located that a sector of it lies in the trough formed by these screens. The two outer screens, which produce pictures of the two opposite sides of the tire sector, are each associated with two or three mirrors at such angles as to reflect the pictures to a common axis which is preferably perpendicular to the central or third screen at its center. The central screen is associated with a set of mirrors which reflect the picture of the tire thread out of and back into the same axis with an optical path identical in length to that of the mirrors for the outer or lateral screens.

Since each mirror reverses the image, each pair restores the image to its original posture. The central image, which is closest to the pick-up or camera, cannot easily be returned to the central axis with fewer than three mirrors, which would leave the image reversed. A more compact arrangement with four mirrors avoids reversal and gathers more light in an optical lens of given aperture. The lateral images can then be directed in optical paths of the same length into the axis of a fixed focus lens either by two mirrors which present erect images or by three mirrors presenting reversed images requiring electronic rereversal. The camera tube, optically coupled to the lens, either with or without a light intensifier, will then transmit to the storage tube at successive short intervals the three images making up the desired composite picture.

The foregoing arrangement of three optical paths preferably involves a mirror in the same location in front of the optical lens of a television camera, but facing in a different direction for each of the three paths from the three fluorescent screens. This is accomplished by using a single mirror which is turned into three positions one after the other as each sector of the tire is being examined.

The three electronic images successively produced in the camera tube for the three portions of each tire sector are then transferred each to one-third the width of the target of a storage tube. The composite image of the entire width of a tire sector is read out of the storage tube for display on the picture tube of a television monitor as a still picture.

During display of the composite picture of a bead to bead sector of a tire, by reading out the entire electronic image in the storage tube to a picture tube as a still picture, the tire is rotated by a predetermined angle to bring another sector into the X-ray beam; and images of the center and two sides are formed in the same manner and transferred each to one-third the width of the target of a second storage tube. Then this composite image replaces the previous one on the picture tube of the monitor while the tire is rotated to a third position for production of the next composite image in the first storage tube, and so on alternately, until the entire circumference has been examined.

If desired, two or more composite images can be displayed simultaneously on the monitor, since they are several times as wide as they are high, and as many as three of these composite strip pictures will fit the usual oblong shape of the picture tube. This will require additional storage tubes, numbering one more than the number of images displayed, and addition of conventional switching circuits to move each picture into another band of the picture area of the television monitor, until it has been displayed in each of the two or three positions. Such multiple display can be helpful in permitting an operator to observe a minor irregularity for a longer time, or to follow a major irregularity as it progresses across more than one of the composite strip pictures.

DETAILED DESCRIPTION OF INVENTION

Figure 1:
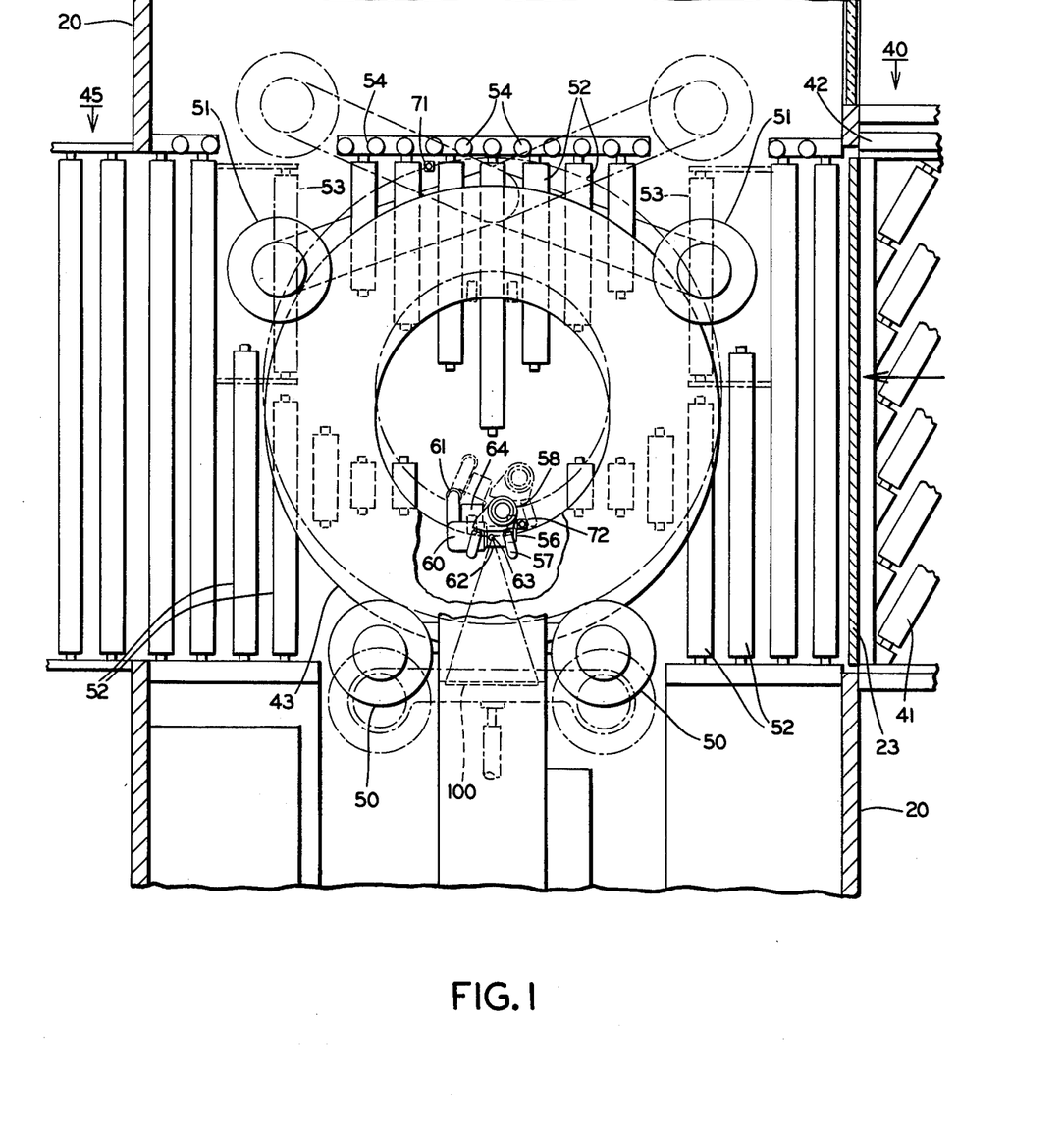
FIG. 1 is a plan view showing primarily the tire handling mechanism.
Figure 2:
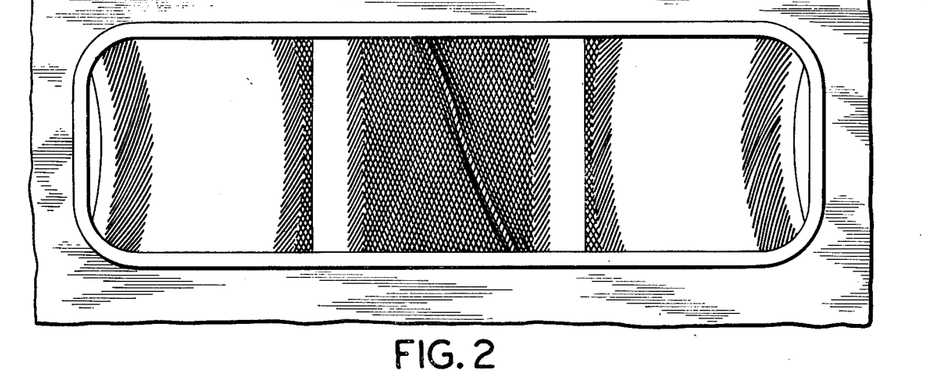
FIG. 2 is a typical composite picture of one tire sector, as it appears on a television monitor.
Figure 3:
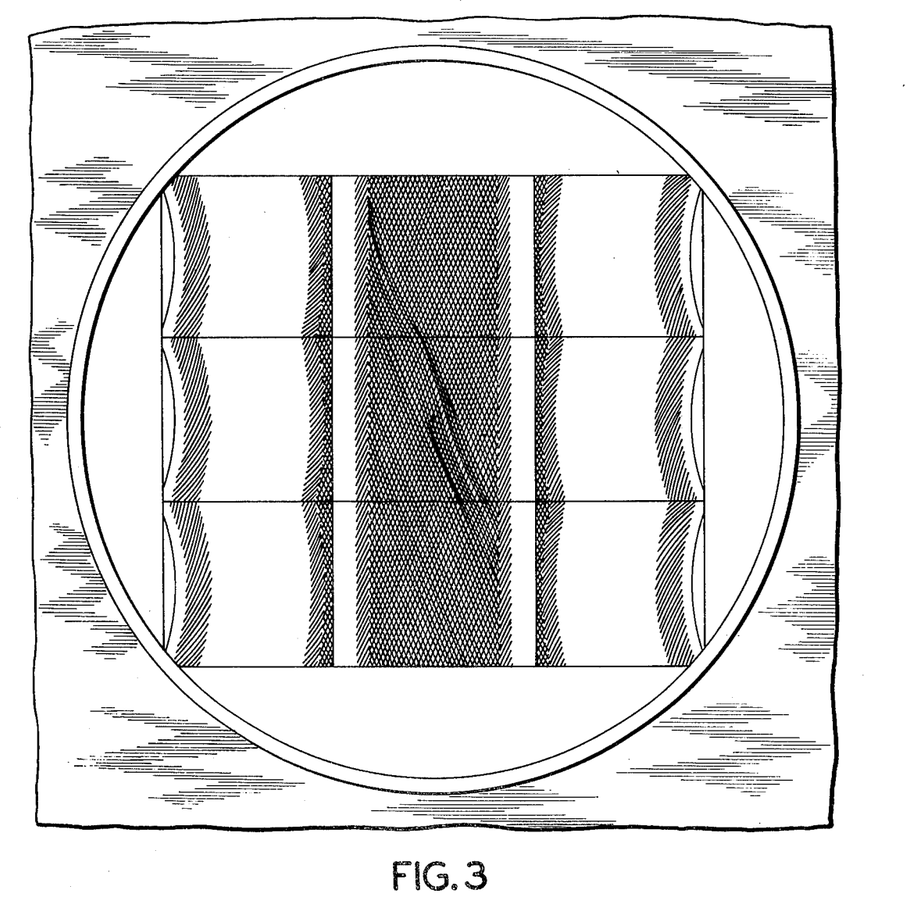
FIG. 3 is a typical composite picture of three adjacent tire sectors, as it appears on a television monitor.

Referring to FIG. 1, the tire inspection machine includes the usual lead shielded enclosure 20, within which may be placed the necessary X-ray transformer, coolant supply, and an air-conditioner. On one side is a vertically sliding entrance gate 23 arranged for admission of one tire at a time.

On the same side as the entrance gate 23 is the supply conveyor 40 which may be a conventional gravity or power-driven roller conveyor terminating in a short section adjacent to the gate 23 provided with skewed rollers 41 facing diagonally toward a lateral fence 42, against which each tire, in turn, is brought to rest by the skewed rollers. On the opposite side of the machine is the exit conveyor 45, which may also be a roller conveyor, and may include a short section of conveyor, which can be tilted downward for diversion of defective tires out of the production line.

Within the shielded room 20 are a pair of transversely linearly movable spools 50 with vertical axes and another pair of arcuately movable spools 51, each of which can be withdrawn out of the path of the tires entering the machine and can be advanced into the path of the tires to engage each of them in turn and hold it for examination.

Clusters of short rollers 52 occupy spaces out of the paths of the spools 50 and 51 to support the tires entering and leaving the machine. These rollers are power driven to advance the tires to the proper position and to remove the tires on completion of the examination. Other short rollers 53 on swing arms are placed in the gaps between the clusters of rollers 52 during motion of tires into and out of the machine, but are withdrawn out of the paths of spools 50 and 51 at other times. On the same side of the path of the tires as the fence 42 and the arcuately movable spools 51 is an array of vertical rollers 54, to guide the tires directly across the machine.

Mounted either above or below the path of the tires, but movable vertically into the path, are a bead spreader mechanism 56 and an X-ray source 60. Between the linearly movable spools 50 is an X-ray imaging system 100 which will be described in more detail below.

The bead spreader mechanism 56 is of the general type shown in U.S. Pat. No. 3,789,226 mentioned above. It consists of two pairs of fingers 57, freely rotatable about horizontal axes, and supported by telescoping tubes 58. The upper pair of fingers 57 may be mounted on an outer supporting tube or tubes, and the lower pair of fingers on an inner tube or tubes 58, with the fingers 57 of each pair spaced horizontally far enough to be out of the X-ray beam from the X-ray source 60. They are also on such a horizontal angle as to be approximately radial to the tires being examined. The entire bead spreader mechanism 56 is power driven for vertical motion into the open center of the horizontal tire in the machine and for moving the fingers 57 horizontally into the space between the beads of the tire. The beads are spread by vertical separation of the upper pair and lower pair of fingers 56 by telescoping motion of the supports 58, as described in greater detail in the aforementioned patent.

The X-ray source 60 is mounted on a vertical arm 61, containing the necessary electric cables. This arm is vertically movable to place the window of the X-ray tube 62 within the open bead circle of a tire, in the central plane of the tire, and to move the tube horizontally to position the X-ray source close to or between the beads of the tire, for which purpose the X-ray tube 62 is offset from the supporting arm 61. The X-ray tube 62 is preferably of the type which is rotatable on its longitudinal axis by a suitable power drive such as a stepping motor 64 to direct the X-ray beam from the window 63 in various directions.

In this machine, the tires to be examined, regardless of size, are placed with their midplanes at a predetermined level, and the X-ray source is introduced into the center of the tire, with its window in the midplane, close to the tire beads but not between them. This is accomplished by the combined sequential action of a series of mechanisms.

The first in order of the positioning mechanisms is an electric eye 71 near the vertical rollers 54 and just beyond the center of the machine. When the tire moving along the rollers 54 interrupts the beam, the drive for conveyor rollers 52 is stopped, removable rollers 53 are dropped, and spools 51 are swung inward, pushing the tire in front of them. Another electric eye 72 near the position of the X-ray source 60, has its beam first interrupted by the tire and then shining through the open center of the tire when the tire is near its desired location between the entrance and exit. The illumination of the electric eye 72 after the temporary interruption of the light beam stops advance of spools 51 and starts advance of spools 50 toward the tire from the side away from the rollers 53.

When the linearly movable spools 50 engage the tread of the tire with a predetermined force, the reaction triggers discontinuance of motion of the spools, and commencement of lift of the tire by the flanges 55 of spools 50 and 51. At the same time the distance between the bead circle and the tread of the tire (that is, the section height of the tire) is sensed by a motion measuring device such as a pulse generator attached to the power drive of spools 50 and an associated pulse counter. The distance so measured is used for automatic control of further functions of the machine, as will be explained below.

Figure 13:
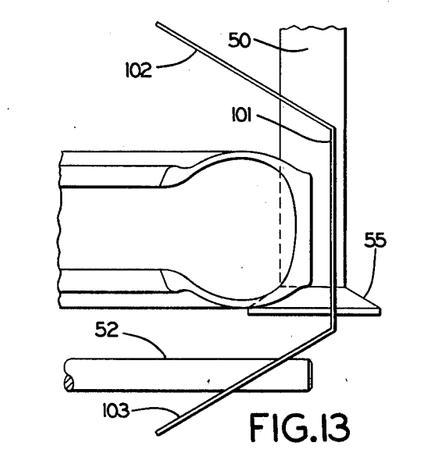
FIG. 13 is a diagrammatic view of the tire lifted from the rollers by the flanged spool.

The spools 50 and 51 are equipped with power driven vertically movable lower flanges 55 and also with stepping motors for periodically rotating the spools, all of which are also described in U.S. Pat. No. 3,789,226. The flanges 55 are lifted to an extent which will place the midplane of the tire opposite to the center of the imaging system. If the tires all have the same height/width ratio, the extent of lift is easily programmed from the section height sensed in the manner just explained. If they are of varying height/width ratios, better results are obtained by driving both upper and lower flanges of spools 50 and 51 toward one another at the same speed until a fixed resistance is encountered, which will position almost all sizes and kinds of tires with their midplanes accurately located in a position corresponding to the subsequent location of the X-ray source 60, as shown in FIG. 13.

Figure 14:
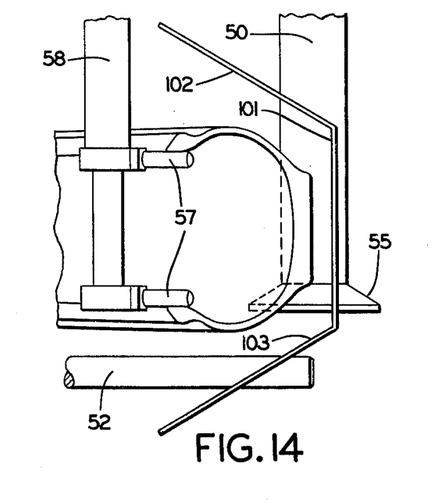
FIG. 14 is a diagrammatic view of the tire with its beads spread, ready for positioning of an X-ray source for examination of the inner structure.

When the lifting motion of the tire is completed, the bead spreader mechanism 56 is moved vertically to the predetermined elevation just mentioned, and then horizontally to place the fingers 57 between the tire beads. The pairs of fingers are then separated vertically to spread the beads by an amount proportional to section width, which amount is also derived from the section height of the tire, as explained above. The position and condition of the tire at this stage are shown in FIG. 14.

Finally, the X-ray source 60 is moved vertically so that the axis of the X-ray tube 62, including the target which is the source of the X-ray beam, is in the same predetermined plane as the central plane of the tire. The X-ray source 60 is then moved horizontally toward the imaging system 100, with the longitudinal axis of the X-ray tube parallel to each of the fluorescent screens of the imaging system, which will be described below. By suitable timing of the stepping motor 64, the X-ray tube can be turned to project the X-ray beam successively through one bead and sidewall of the tire being examined, then through the tread portion, and finally through the other sidewall and bead. With a period of rest in each of these three positions, a fourth period of approximately equal length is conveniently used for turning the tire which is being examined, to advance another sector into the path of the X-ray beam, by rotation in unison of all the spools 50 and 51 through a predetermined angle.

These time periods for projecting the X-ray beam through different areas of a tire match those for establishing different optical paths from one or another of the fluorescent screens, so that the X-ray beam will always be directed toward the one of the three fluorescent screens for which a complete light path into the video camera 105 is then provided, as will be explained below.

The imaging system 100 has its primary axis in the same predetermined plane already mentioned, which is also the central plane of the tire when the tire is properly positioned.

The first element of the imaging system is a group of fluorescent screens, preferably three in number. A central fluorescent screen 101 is perpendicular to the central plane of the tire for receiving a shadow picture of the tread or crown portion of the tire, and is flanked by an upper fluorescent screen 102 and a lower fluorescent screen 103, above and below the tire, at an angle in each case of about 60° to 75° to the plane of central screen 101. Screens 102 and 103 receive shadow pictures of the two sides of the tire.

The fluorescent screens and the other structurally connected elements of the imaging system are enclosed in a light-tight compartment in the usual manner, to prevent stray light from interfering with functioning of the system, but for simplicity of illustration, the enclosure is omitted from the drawing.

The imaging system also includes at least one video camera for transmitting the shadow pictures on the several fluorescent screens. The structurally simplest arrangement is to provide the same number of cameras as screens, with each camera directed to a single screen, and with conventional circuitry for transferring the electronic image from each camera to a part of the target of a storage tube to compose a composite picture which is then read out on the picture tube of a monitor. Such an arrangement is subject to variations in transmission of the partial images making up the composite picture and it is therefore preferred to use a single video camera, particularly since the cameras are actually used for only a fraction of the total time consumed, with the remainder of the time taken up by viewing of the composite picture by an operator, and in part by shifting of the position of the tire for presentation of another sector for examination.

Figures 4, 5, 6, 7, 16:
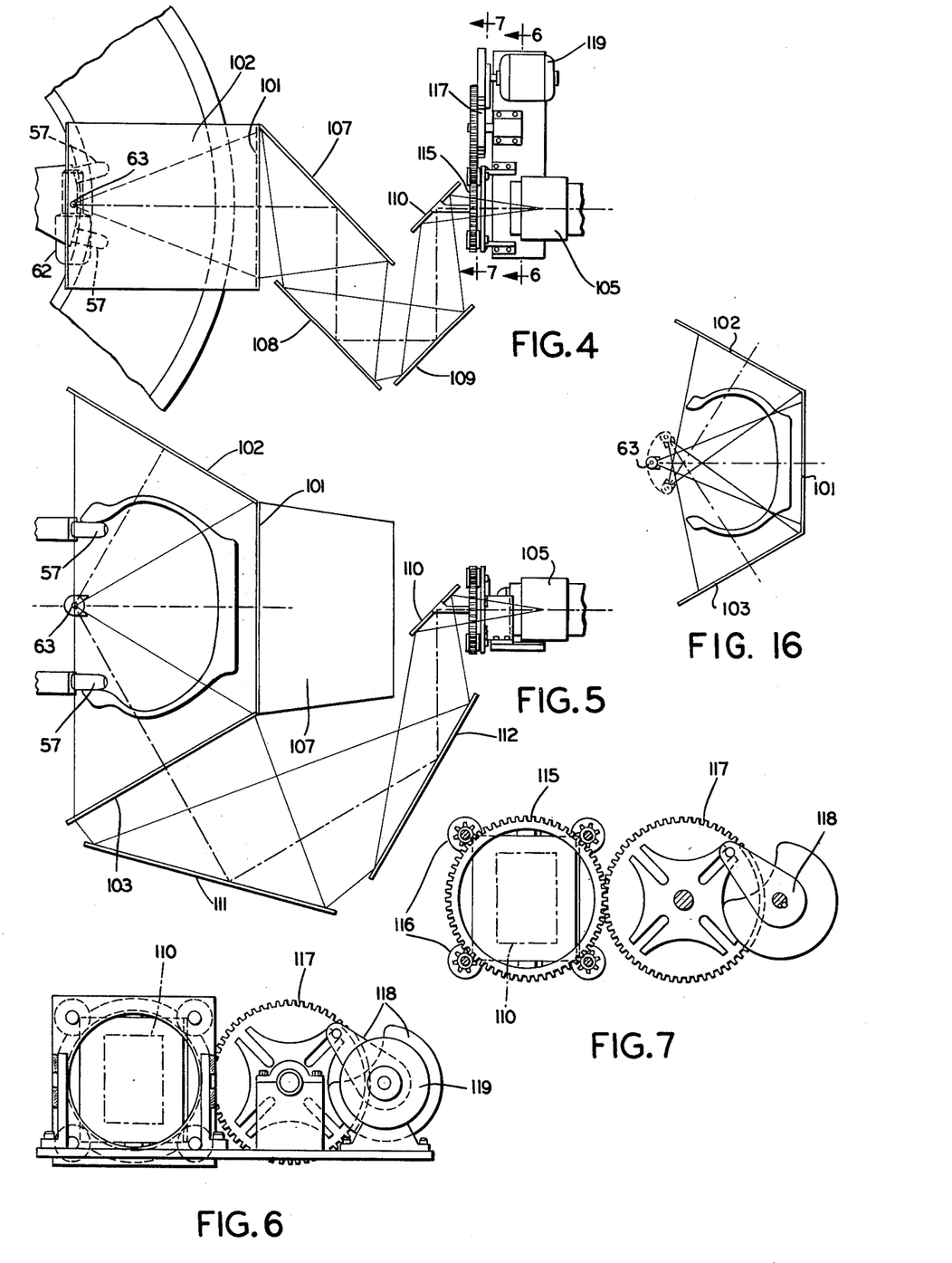
FIG. 4 is a diagrammatic plan view of one form of imaging system involving an even number of mirrors for the central optical path.
FIG. 5 is a similar diagrammatic side view of the same imaging system involving odd numbers of mirrors for the lateral optical paths.
FIG. 6 is a large scale view of the support and drive for the rotating mirror common to the optical paths of FIG. 4 and FIG. 5.
FIG. 7 is a view similar to FIG. 6, omitting supports to show more clearly the mode of action of the mirror drive.
FIG. 16 is a diagrammatic representation on a somewhat reduced scale of an arrangement which assures avoidance of any gaps in the images.

In a preferred embodiment illustrated in FIGS. 4 and 5, a highly sensitive video camera with a wide aperture lens is mounted in alignment with the center of screen 101. Immediately behind the screen 101 at a 45° angle, as shown in FIG. 4, is a mirror 107 reflecting the image on fluorescent screen 101 to one side, and as close to it as is possible without interference is a second mirror 108 parallel to mirror 107 to reflect the image in a direction parallel to the original light path. A third mirror 109 at a right angle to mirror 108 reflects the image back toward the axis of the device and a fourth mirror 110 parallel to mirror 109 completes the reflective system so that the camera 105 views the shadow picture on the fluorescent screen 101 as though it were viewed directly from a distance such as to produce a very small electronic image in the camera, but in a camera location much closer than that distance, because of the folding of the light path by the successive reflections. Mirrors 107, 108, and 109 are in fixed positions, but mirror 110 is rotatable, as will be explained below.

Fluorescent screens 102 and 103 on the two sides of the tire are each associated with identical sets of mirrors, but only the set for lower screen 103 is shown in FIG. 5. In this set there are three mirrors between the fluorescent screen 103 and the camera 105 rather than the four between screen 101 and the camera 105. The first mirror 111 closest to the fluorescent screen 103 is placed as close to the screen as it conveniently can be without encountering interference from mirror 107, and reflects the shadow picture on screen 103 at approximately a right angle. A short distance behind the mirror 107 there is another mirror 112 reflecting the shadow picture at a quite obtuse angle, so that the reflected light path, or optical axis, is perpendicular to the axis of camera 105, and reaches mirror 110 in such a manner as to be reflected accurately along the optical axis of camera 105. By adjusting the exact position and angle of mirrors 111 and 112, the length of the light path can be made equal to that from screen 101 to camera 105 so that the images from both screens 101 and 103 can be accurately focused at the same setting of the optical lens of camera 105. The same is true of the image from upper screen 102, since its light path has the same shape and length as that from lower screen 103.

As has already been stated, mirror 110 is common to the optical system for all three fluorescent screens 101, 102 and 103, but has to be turned in a different direction to receive and transmit the light from each of those screens. This is accomplished by mounting mirror 110 at a 45° angle on a ring gear 115, as shown in FIGS. 6 and 7. The ring gear 115 turns within a group of supporting wheels 116, mounted on a common support with the video camera 105. The ring gear 115 meshes with an equal size driving gear 117, forming part of a four-branched Geneva drive mechanism, of which the cam and pin element 118 is connected to a constant speed motor 119. Consequently, the mirror 110 will successively take four stationary positions at right angles, with a brief interval for shifting from one position to the next. If desired, a stepping motor can be used for the same purpose, but the Geneva drive is presently preferred for accurate placement of mirror 110 in its three operative positions.

In three of its four positions, rotatable mirror 110 forms part of the light path from one or another of the three fluorescent screens in turn, and in its fourth position is inoperative. In this dead position, time is provided for moving the tire by rotation of the four spools 50 and 51 through such angles as to bring another sector of the tire into position to intercept the X-ray beam so that the shadow picture of that new sector can be received by the video camera 105.

It should be noted that the optical system, including the screen 101, involves four mirrors, each of which reverses the picture so that the repeated reversal and rereversal restore the picture viewed by the camera 105 to an upright posture, but that the three mirrors reflecting the pictures on the upper screen 102 and the lower screen 103 leave the picture reversed from top to bottom, which means from one side of the tire to the other. This requires an additional reversal operation before the three part-images can be brought together to compose a composite image of the entire sector from bead to bead of the tire with the parts in proper sequential order. This operation is easily performed by conventional electronic means for choosing the proper direction of scan when reading out each partial image from the camera 105 for transfer to the further processing elements of the viewing equipment.

The video camera 105 necessarily includes at least an optical lens focused on a light sensitive surface on which an electric charge proportional to the illumination is formed. It can include also various refinements and amplification elements such as a preliminary light intensifier or internal electronic charge amplifiers. In any event, since the contrast in the shadow picture of the tire is likely not to be very great, the camera should be of a type which will provide for maximum sensitivity to small variations in intensity of illumination. Moreover, it should be of a type which integrates the charge so as to produce an ultimate electronic image of maximum clarity and definition in viewing the shadow picture of the stationary tire sector.

Figure 8:
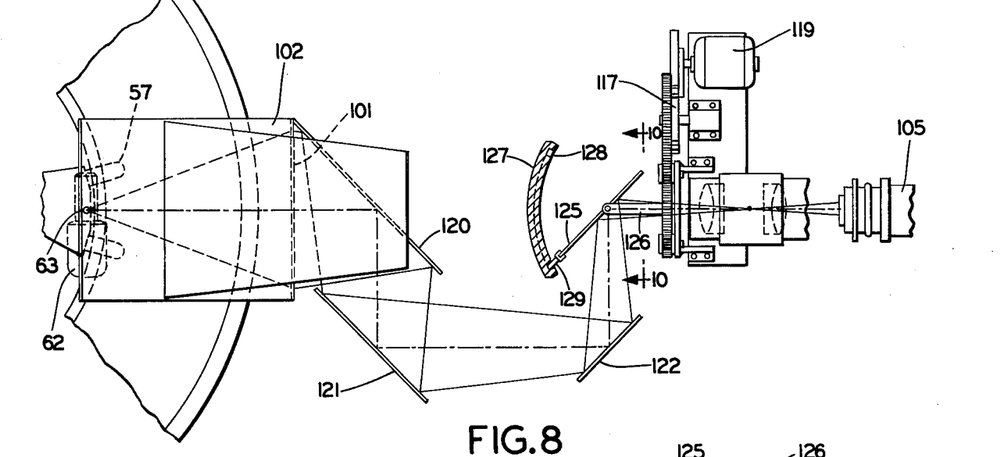
FIG. 8 is a diagrammatic view of another form of imaging system involving an even number or mirrors for the central optical path.
Figures 9, 10, 11:
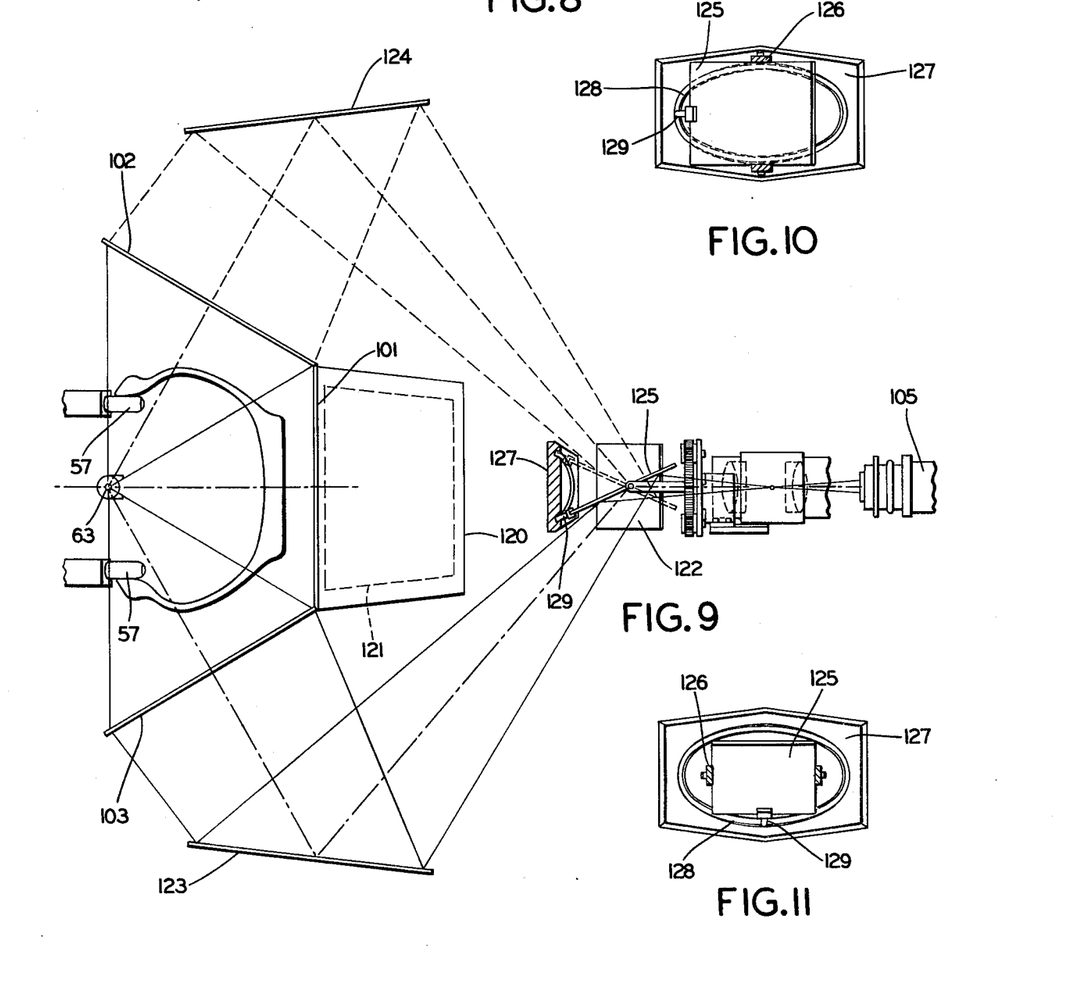
FIG. 9 is a similar diagrammatic view of the same form of imaging system as FIG. 8 having an even (rather than odd) number of mirrors for the lateral optical paths.
FIG. 10 is an enlarged view of the common mirror of FIG. 8 and FIG. 9 showing how a cam positions it for the optical path of FIG. 8.
FIG. 11 is a view similar to FIG. 10 showing the common mirror positioned for the optical path of FIG. 9.
Figure 12:
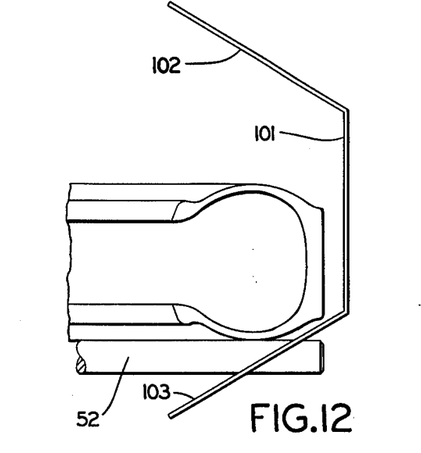
FIG. 12 is a diagrammatic view of a tire resting on the supporting rollers when the motion of the tire has just stopped.

An alternative arrangement for producing successive optical images of three adjacent fluorescent screens in a video camera is shown in FIG. 8 and FIG. 9. In this embodiment, as in the one already described, the sector of tire undergoing examination is surrounded by three fluorescent screens 101, 102 and 103, and a video camera 105 is in alignment with the center of the central screen 101, as described above.

The optical path from the central fluorescent screen 101 to the video camera 105 resembles that of FIG. 4, including four mirrors, each at a 45° angle to the optical axis so that the light is reflected at right angles to its previous path and then returned to the original axis a short distance away. These four mirrors again include three stationary mirrors 120, 121 and 122, in order, from the fluorescent screen 101 toward the video camera 105. The fourth mirror 125 is a movable mirror, but with a more complex motion than that of mirror 110.

In this arrangement, the light paths from the upper screen 102 and the lower screen 103 to the camera 105 each includes only two mirrors. Thus, in FIG. 9, the shadow picture on the lower fluorescent screen 103 is reflected by a stationary mirror 123, and that on the upper fluorescent screen 102 is reflected by a stationary mirror 124, in each case directly to the movable mirror 125. Since there are only two mirrors, the shadow picture is rereversed and the image received from each of the three fluorescent screens 101, 102 and 103 is in an upright position in each instance. However, bringing about this result not only requires a longer light path in avoiding interference with mirror 121, with a resulting loss of light intensity, but also for a light path of reasonable length it requires placement of the mirrors reflecting the shadow pictures on the upper and lower screens 102 and 103 at odd angles so that there is no right angle reflection. Accordingly, the movable mirror 125 not only must be rotated to receive light from the proper side of the axis of the camera 105, but must also be tilted to accommodate the odd angle of reception of the light just mentioned.

The tilting of the mirror 125 requires an additional mechanism illustrated particularly in FIGS. 8 to 11. As in the case of the mirror 110, shown in FIGS. 4 through 7, mirror 125 is mounted on a ring gear driven by a Geneva drive mechanism, but in this case the mirror 125 is not solidly mounted, but it is pivoted in a yoke 126. A stationary cam plate 127 is provided which has the shape of a portion of a sphere, on which is cut a cam track 128. The cam track 128 can be either oval as shown in FIG. 9 or in an egg shape, with one half circular and the other half ellipsoidal. Thus in the part of a cycle of operation in which the mirror 125 is reflecting the shadow picture from fluorescent screen 101, it is required to be at a 45° angle to the axis of camera 105 for a right angle reflection, and the mirror 125 is placed at that angle by cam follower 129, riding track 128 to one of the extremities of the oval shown in FIG. 8 and FIG. 10 (or to the extremity of the ellipsoidal half of an egg-shaped track, if used). In the preceding and following parts of the cycle, when the mirror 125 is reflecting the shadow picture from upper screen 102 or lower screen 103, it is required to be at a more acute angle to the axis of camera 105 for an obtuse angle reflection, and cam follower 129 will be in one of the parts of the track in which track 128 is closer to the axis of the device, as shown in FIG. 9 and FIG. 11. As was previously explained, one-fourth of the cycle is used for advancing the tire to a new position and no reading is taken during that part of the cycle. Consequently, it makes no difference what the shape of the cam track is during the dead one-fourth of the cycle and the track can follow a simple circular path (as part of an egg shape) to the next live position.

Still other optical systems can be used for viewing of the several fluorescent screens. For example, mirrors adjacent to each fluorescent screen may be placed for reflection horizontally, in the same direction as that of entrance and exit conveyors 40 and 45, with second and third mirrors for reflection into a horizontal camera axis, also parallel to the conveyors and passing through or close to the X-ray source. Such an arrangement would produce optical images tilted sideways at the same angles as the fluorescent screens, and require turning of the camera for alignment with the plane in which the folded optical axis lies for each partial image, or else provision of a rotatable reversing prism such as is used in panoramic telescopes.

In both of the embodiments of optical systems illustrated in the drawings and specifically described above, successive images of three parts of the width of a sector of a tire are produced in a single video camera, for subsequent processing into a composite image for display to an operator or observer, as will be described further below.

The production of such a composite picture can be brought about in various alternative ways. One way, as has already been mentioned, is to provide three video cameras, a separate one trained on each fluorescent screen. Still another is to reflect the shadow pictures from the several fluorescent screens to a common location in one of the ways shown, but instead of having a rotating mirror reflect the pictures successively into the axis of a camera, a cluster of mirrors can be provided, with each at such an angle as to receive the light from one fluorescent screen and reflect it into a single camera in such a manner as to impinge on one-third of the width of the light sensitive plate of the camera.

Best results have been obtained by producing separate electronic images successively in a single video camera and combining them by transfer of each image in turn to one-third of the width of the target of a storage tube to compose the desired composite picture in the storage tube, which can be at another more convenient location than that of the camera.

If it is found to be inconvenient to obtain partial images which exactly match at their edges, because of physical problems of bringing edges of the several fluorescent screens exactly together, or of reproducing the images with their edges exactly coinciding, or if it is desired to produce partial images which will have slightly overlapping edges for some other reason, it may be preferred to have the X-ray source for the several partial images slightly displaced from a common point of origin, in a direction away from the screens as shown in FIG. 16. For this purpose, it is only necessary to mount the X-ray tube in its rotating support slightly off center so that the focal spot will be slightly farther from the fluorescent screen in each position than the axis of rotation of the X-ray tube.

In every case, the tire which is being examined must be turned stepwise to advance one sector of the tire after another into viewing position. The circumferential distance of advance of the tire from one viewing position to the next is governed by the width of the screens 101, 102, and 103, and determines the angle of rotation of spools 50 and 51 in each step. The number of steps is governed by the circumference of the tire, which depends on bead diameter and section height. With tires of the same bead diameter, the number of steps is derived by a very simple computation from the constant bead diameter and variable section height, the latter being determined from the reading of the position to which spools 50 were advanced, as already described. Accordingly, instructions based on the extent of advance of spools 50 can be automatically converted into instructions for the number of steps of rotation of the four stepping motors driving the supporting and tire indexing spools 50 and 51.

If tires of differing bead diameters are to be handled, an additional measurement may be required, which can be carried out automatically by such means as those set forth in U.S. Pat. No. 3,789,226.

After the proper number of steps, of the proper circumferential distance each, the programming equipment causes retraction of the X-ray source, convergence of the bead spreader fingers, retraction of the bead spreader, and finally lowering of the spool flanges 55 to deposit the tire on conveyor rollers 52 for conveyance out of the machine.

Figure 15:
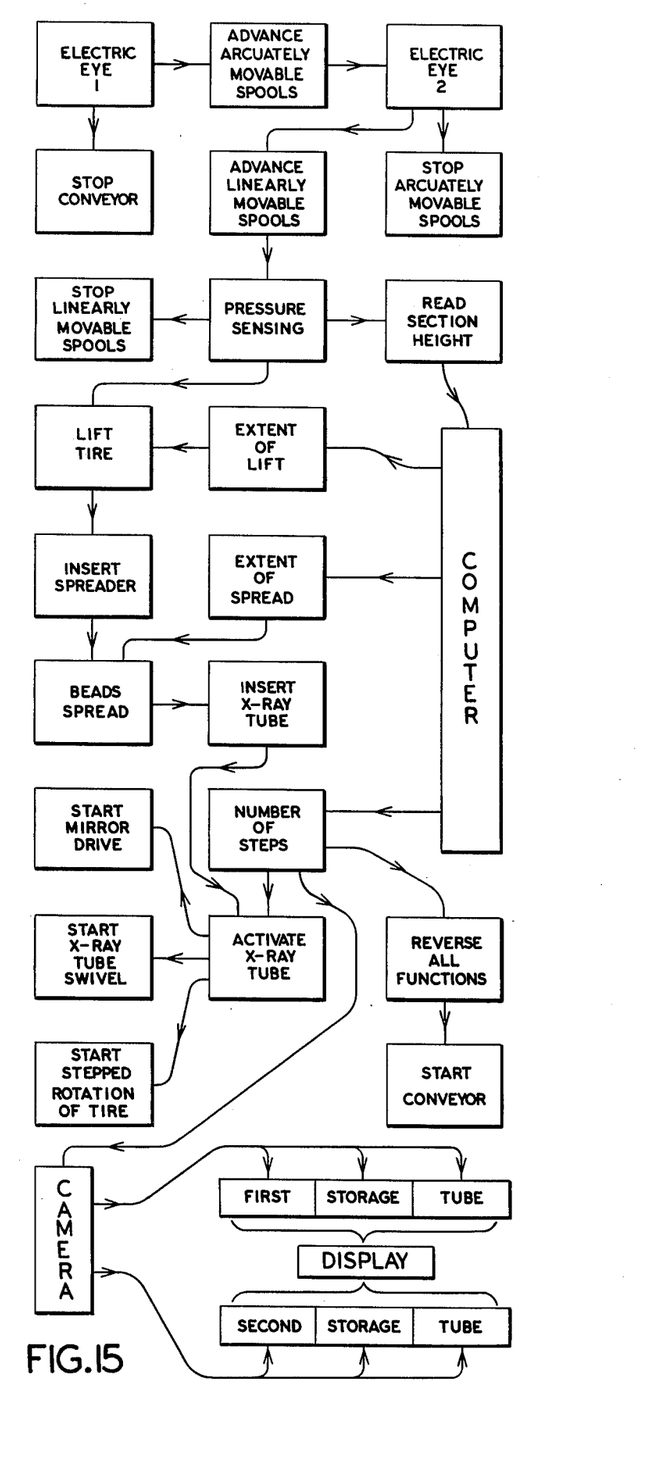
FIG. 15 is a schematic diagram of interconnections between the elements of the machine.

Accordingly, in the preferred form of this invention, timing or programming equipment is provided for receiving the electric eye signal of the presence of a tire and performing the following operations, as indicated in the diagrammatic chart of FIG. 15.

- A. Electric eye 71 stops the conveyor, drops rollers 53 out of the way, and starts advance of spools 51.
- B. Electric eye 72 stops advance of spools 51 and starts advance of spools 50.
- C. Reaction pressure of tire against spools 50 stops their advance, starts simultaneous lift of bottom flanges of spools 50 and 51 and also causes position of spools 50 to be read into a computer or other programming device.
- D. Computer translates position of spools 50 into desired distance of lift of tire, extent of spread of beads, and number of steps for a complete rotation of the tire being examined.
- E. Flanges of spools 50 and 51 lift tire the determined distance.
- F. Bead spreader 56 moves vertically to the central plane, and horizontally placing fingers 57 between beads.
- G. Bead spreader fingers 57 separate to spread beads the determined distance.
- H. X-ray source 60 moves vertically to the central plane, and horizontally to a position near the beads (with window 63 turned toward upper fluorescent screen 102 and with mirror 110 turned to reflect an image from that screen).
- J. 1. With X-rays emanating from the window forming a shadow picture of one side of a tire sector and a corresponding electronic image in the video camera, the image is transferred to one-third of the width of the target of a storage tube.
  2. The constant speed motor 119 through Geneva drive 118 turns mirror 110 a quarter turn to reflect the shadow picture of the center of the tire sector.
  3. Simultaneously with turning of mirror 110, stepping motor 64 turns X-ray window 63 toward the center screen.
  4. The image of the shadow picture on the central screen is transferred to the center of the target of the storage tube.
  5. The constant speed motor turns mirror 110 another quarter turn.
  6. The X-ray window is turned toward the lower fluorescent screen.
  7. The image of the shadow picture on the lower screen is transferred to the last third of the width of the target of the storage tube.
  8. The constant speed motor turns mirror 110 a quarter turn to a dead or inoperative position.
  9. The X-ray window is turned to its starting position.
  10. The composite image in the storage tube is read out as a still picture on a television monitor.
  11. Spools 50 and 51 turn a determined angle to advance another tire sector in viewing position.
  12. The constant speed motor turns mirror 110 a quarter turn to its starting position.
  13. to 24.
  Steps 1 to 12 are repeated with the composite image being formed in a second storage tube, while the previous image continues to be displayed through steps 13 to 21. In step 22, the picture from the first storage tube is replaced on the monitor by the picture from the second storage tube.
  25., et seq.
  Steps 1 to 24 are repeated, with the picture from the second storage tube being displayed through the first nine steps.
- K. After stepwise turning of the tire by the determined number of steps for exposure of every sector for inspection, and completion of the 12th (or 24th) step of operation J, the X-ray tube is moved horizontally into the center of the tire, and is withdrawn vertically.
- L. The bead spreader fingers are brought together.
- M. The bead spreader is moved horizontally into the center of the tire, and is withdrawn vertically.
- N. Spool flanges 55 are lowered to deposit the tire on conveyor rollers 52.
- O. Spools 50 and 51 are retracted, and the retracted rollers 53 are replaced.
- P. The tire exits.
- Q. Gate 23 admits another tire onto rollers 52.
- R. The tire is stopped on signal from the electric eye, and another cycle starts.

The entire sequence of steps J-1 to 12 can be carried out in only a second or two, which is sufficiently long for an observer, looking at a sharp still picture on the picture tube of the monitor, to detect the presence of irregularities, and to operate a control for marking the tire and diverting it from the production line for special handling. Since the number of sectors required to be exposed may be from about a dozen to twice that many, for common tire sizes, it is apparent that the complete examination of a tire can be conducted in well under a minute. The operator will than have a brief rest while the machine discharges the tire and prepares to present another one for inspection. The total time of about a minute or less for small sizes, or not much over a minute for the larger truck tire sizes, makes this machine especially useful for 100% inspection production line operation.

The actual formation of the composite image requires only conventional switching circuits with the conventional timing devices and adjustments for reading out the electronic image in the video camera at the proper moment for transfer to the storage tube, and specifically for transfer of each partial image to the designated part of the target of the storage tube during the time period in which the partial image is present in the video camera 105.

The present invention permits more complete inspection, or more precise inspection, or more economical inspection, or more rapid inspection than previous X-ray inspection machines because of the rapid sequential presentation to a single operator of still pictures of the entire width of successive sectors of a tire, which has never before been accomplished.

We claim:

1. An X-ray inspection system for a pneumatic tire, comprising:
   a. a support for a tire,
   b. means for stepwise rotation of a tire on the support,
   c. a plurality of fluorescent screens extending essentially around the entire width, from bead to bead, of the outside of a sector of a tire on the support,
   d. at least one X-ray source,
   e. means for directing X-rays from the X-ray source to each fluorescent screen in turn through the wall of the said sector of a tire on the support to form essentially adjoining shadow pictures of different parts of the sector of the tire on the several fluorescent screens,
   f. a video camera,
   g. means for exposing the video camera to each fluorescent screen in turn through paths of essentially equal optical length to produce a sequence of electronic images of the said adjoining shadow pictures,
   h. means for transferring the several electronic images in the video camera in turn to adjacent positions in a storage device, to produce an essentially complete composite image of the said sector of a tire, and
   i. means for displaying the said composite image as a still picture on a monitor.

2. A system as in claim 1, in which the fluorescent screens are placed edge to edge to generate shadow pictures which collectively depict essentially the entire width of the sector of the tire.

3. A system as in claim 2, in which mirrors reflect the shadow pictures on the several fluorescent screens into a single video camera.

4. A system as in claim 3, in which a mirror adjacent to the video camera is provided with means for stepwise rotation to positions for reflecting the images from the several fluorescent screens in turn.

5. A system as in claim 4, in which the optical path from each fluorescent screen through the mirrors to the video camera is in a single plane.

6. A system as in claim 5, in which an X-ray source is positioned so that the axis of the X-ray beam directed to each fluorescent screen crosses the axis of each of the X-ray beams directed to the other screens.

7. A system as in claim 5, including means for stepwise positioning of the tire for successive exposure of different sectors.

8. A system as in claim 7, in which composite images are received alternately in different storage devices with the image on one storage device being displayed continuously during the entire interval for composing a composite image in another storage device and for moving the tire to a position for exposing another sector of the tire.

9. A system as in claim 8, including means for display of two successive composite images simultaneously on adjacent bands of a single monitor.

* * * * *